(12) United States Patent
Scheunemann et al.

(10) Patent No.: US 10,933,005 B2
(45) Date of Patent: Mar. 2, 2021

(54) POWERFUL HAIR TREATMENT AGENT HAVING ANTI-WASHOUT EFFECT

(71) Applicant: Henkel AG & Co. KGaA, Duesseldorf (DE)

(72) Inventors: Volker Scheunemann, Lueneburg (DE); Erik Schulze zur Wiesche, Hamburg (DE); Rene Krohn, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/363,361

(22) Filed: Nov. 29, 2016

(65) Prior Publication Data
US 2017/0151145 A1   Jun. 1, 2017

(30) Foreign Application Priority Data

Dec. 1, 2015 (DE) ...................... 10 2015 223 839.3

(51) Int. Cl.
| | | |
|---|---|---|
| *A61Q 5/00* | (2006.01) | |
| *A61Q 5/12* | (2006.01) | |
| *A61K 8/36* | (2006.01) | |
| *A61K 8/362* | (2006.01) | |
| *A61K 8/46* | (2006.01) | |
| *A61K 8/365* | (2006.01) | |
| *A61K 8/23* | (2006.01) | |
| *A61K 33/38* | (2006.01) | |
| *A61K 8/19* | (2006.01) | |
| *A61K 8/25* | (2006.01) | |
| *A61K 8/42* | (2006.01) | |
| *A61Q 5/02* | (2006.01) | |

(52) U.S. Cl.
CPC ............... *A61K 8/466* (2013.01); *A61K 8/19* (2013.01); *A61K 8/23* (2013.01); *A61K 8/25* (2013.01); *A61K 8/36* (2013.01); *A61K 8/362* (2013.01); *A61K 8/365* (2013.01); *A61K 8/42* (2013.01); *A61K 33/38* (2013.01); *A61Q 5/004* (2013.01); *A61Q 5/02* (2013.01); *A61Q 5/12* (2013.01); *A61K 2800/594* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 2005/0198746 | A1* | 9/2005 | Pollack | A61K 8/466 8/405 |
| 2006/0115440 | A1* | 6/2006 | Arata | A61Q 5/02 424/65 |
| 2008/0031842 | A1* | 2/2008 | Kuhlman | A61K 8/8152 424/70.11 |
| 2011/0274640 | A1* | 11/2011 | Schulze Zur Wiesche | A61K 8/64 424/70.13 |

FOREIGN PATENT DOCUMENTS

| | | | | |
|---|---|---|---|---|
| DE | 102006061555 A1 * | 7/2008 | | A61Q 5/12 |
| EP | 2438900 A1 | 4/2012 | | |

OTHER PUBLICATIONS

DE102006061555 Eng Tran. (Year: 2008).*

* cited by examiner

*Primary Examiner* — Nicole P Babson
*Assistant Examiner* — Lori K Mattison
(74) *Attorney, Agent, or Firm* — Lorenz & Kopf, LLP

(57) ABSTRACT

Hair treatment agents and methods for treating hair using the hair treatment agents are provided. In an embodiment, a hair treatment agent comprises: at least one anionic surfactant from the group of a-olefin sulfonates; at least one anionic surfactant from the group of taurides; at least one amphoteric surfactant; at least one silver salt selected from silver acetate, silver adipate, silver citrate, silver galactarate, silver gluconate, silver lactate, silver malate, silver mandelate, silver salicylate, silver succinate, silver sulfate, and silver tartrate; and at least one organic acid selected from adipic acid, succinic acid, citric acid, acetic acid, galactaric acid, gluconic acid, malic acid, mandelic acid, lactic acid, salicylic acid, sulfuric acid, silver acetate, and tartaric acid, to reduce or prevent washing out of color from dyed hair.

4 Claims, No Drawings
Specification includes a Sequence Listing.

POWERFUL HAIR TREATMENT AGENT HAVING ANTI-WASHOUT EFFECT

CROSS-REFERENCE TO RELATED APPLICATION

This application claims priority to German Patent Application No. 10 2015 223 839.3, filed Dec. 1, 2015, which is incorporated herein by reference in its entirety.

TECHNICAL FIELD

The present disclosure relates to hair treatment agents, in particular, shampoos and so-called conditioners, having a combination of active ingredients for gentle and effective hair care.

BACKGROUND

The importance of care products with the longest possible effect has grown, not least of all due to the great stress on hair, for example, due to dyeing or permanent waves and also due to cleaning of hair with shampoos and due to environmental pollution. Such care products have an influence on the natural structure and properties of hair. For example, the wet and dry combability of hair and the hold and body of hair can be optimized, or the hair may be protected from increased split ends, with the use of appropriate care products.

It has therefore long been customary to subject hair to special after-treatments in which the hair is treated with special active ingredients, for example, quaternary ammonium salts or special polymers, usually in the form of a rinse. These treatments result in improved combability, hold, and body of hair while reducing the amount of split ends, depending on the formulation.

Multifunctional cosmetic products are also known in the prior art. In particular, this includes the so-called "two-in-one" shampoos, which not only clean the hair but also condition the hair. Such products are greatly appreciated by consumers because the product performance thereof eliminates the need for at least one procedural step, e.g., conditioning with a traditional hair conditioner.

Similarly, products for altering the natural color of hair play a prominent role in hair cosmetics. Distinctions are made between permanent, semipermanent, and temporary color systems, which are based on chemical and/or natural dyes. Hair colors artificially produced by permanent, semi-permanent, or temporary color systems have a drawback, however, in that these hair colors can undergo undesirable changes, e.g., during or after hair cleaning.

"Undesirable changes" refers here to fading or bleeding, as well as the loss of color brilliance of the shade of color of the hair obtained from the respective dyeing. Environmental impacts and/or the effects of the sun can further intensify these changes.

The use of divalent metal salts in hair dye agents to improve the durability and thus fastness of the dyeing is known from EP 2438900 A1.

There is still a need to provide active ingredients and/or combinations of active ingredients for hair treatment agents having favorable, nourishing properties that also strengthen the bonding of dyes to the hair fibers and thus maintain the fastness of artificially produced hair color, and to further develop hair treatment agents in this regard.

BRIEF SUMMARY

Hair treatment agents and methods for treating hair using the hair treatment agents are provided. In accordance with an exemplary embodiment, a hair treatment agent comprises at least one anionic surfactant from the group of α-olefin sulfonates, at least one anionic surfactant from the group of taurides, at least one amphoteric surfactant, at least one silver salt selected from silver acetate, silver adipate, silver citrate, silver galactarate, silver gluconate, silver lactate, silver malate, silver mandelate, silver salicylate, silver succinate, silver sulfate, and silver tartrate, and at least one organic acid selected from adipic acid, succinic acid, citric acid, acetic acid, galactaric acid, gluconic acid, malic acid, mandelic acid, lactic acid, salicylic acid, sulfuric acid, silver acetate, and tartaric acid.

In accordance with another exemplary embodiment, a method for hair treatment is provided. The method comprises the steps of applying to dry or damp hair a hair treatment agent. The hair treatment agent comprises at least one anionic surfactant from the group of α-olefin sulfonates, at least one anionic surfactant from the group of taurides, at least one amphoteric surfactant, at least one silver salt selected from silver acetate, silver adipate, silver citrate, silver galactarate, silver gluconate, silver lactate, silver malate, silver mandelate, silver salicylate, silver succinate, silver sulfate, and silver tartrate, and at least one organic acid selected from adipic acid, succinic acid, citric acid, acetic acid, galactaric acid, gluconic acid, malic acid, mandelic acid, lactic acid, salicylic acid, sulfuric acid, silver acetate, and tartaric acid. The hair treatment agent is rinsed from the hair after the hair treatment agent has remained on the hair for a period of about 30 to about 300 seconds.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

It has now been discovered that a combination of certain ingredients has an especially positive effect on dyed hair treated therewith and on the hair follicles.

A first embodiment contemplated herein is hair treatment agents containing:
 a) at least one anionic surfactant from the group of α-olefin sulfonates,
 b) at least one anionic surfactant from the group of taurides,
 c) at least one amphoteric surfactant,
 d) at least one silver salt selected from silver acetate, silver adipate, silver citrate, silver galactarate, silver gluconate, silver lactate, silver malate, silver mandelate, silver salicylate, silver succinate, silver sulfate, and silver tartrate, and
 e) at least one organic acid selected from adipic acid, succinic acid, citric acid, acetic acid, galactaric acid, gluconic acid, malic acid, mandelic acid, lactic acid, salicylic acid, sulfuric acid, silver acetate, and tartaric acid.

Hair treatment agents as contemplated herein include, for example, hair shampoos, hair conditioners, conditioning shampoos, hair sprays, hair rinses, hair cures, hair packings, hair tonics, permanent wave fixative solutions, hair dye shampoos, hair dyeing agents, hair setting formulations, hair styling preparations, blow drying lotions, foam solidifiers, hair gels, hair waxes, or combinations thereof. In view of the fact that men are often reluctant to use a plurality of different products and/or to carry out a plurality of application steps, the hair treatment agents contemplated herein are preferably those which men are already using anyway. Preferred agents therefore include shampoos, hair conditioning agents, or hair tonics.

In an exemplary embodiment, the hair treatment agents contain at least one anionic surfactant from the group of α-olefin sulfonates. Olefin sulfonates are preferably obtained by adding $SO_3$ onto olefins of the formula $R^2$—CH=CH—$R^3$ wherein $R^2$ and $R^3$ independently of one another represent H or alkyl residues having one to 20 carbon atoms, with the proviso that $R^2$ and $R^3$ together contain at least six and preferably 10 to 16 carbon atoms.

In an exemplary embodiment, α-olefin sulfonates that result if $R^2$ or $R^3$ denotes hydrogen are used. Typical examples of the olefin sulfonates used are the sulfonation products obtained by reacting $SO_3$ with 1-, 2-butene, 1-, 2-, 3-hexene, 1-, 2-, 3-, 4-octene, 1-, 2-, 3-, 4-, 5-decene, 1-, 2-, 3-, 4-, 5-, 6-dodecene, 1-, 2-, 3-, 4-, 5-, 6-, 7-tetradecene, 1-, 2-, 3-, 4-, 5-, 6-, 7-, 8-hexadecene, 1-, 2-, 3-, 4-, 5-, 6-, 7-, 8-, 9-octadecene, 1-, 2-, 3-, 4-, 5-, 6-, 7-, 8-, 9-, 10-eicosene and 1-, 2-, 3-, 4-, 5-, 6-, 7-, 8-, 9-, 10- and 11-docosene. The sulfonation is followed by a neutralization, after which the olefin sulfonate is present in the mixture as an alkali metal, alkaline earth metal, ammonium, alkyl ammonium, alkanolammonium or glucammonium salt and preferably as a sodium salt. It is possible to use both paste-form aqueous olefin sulfonates, preferably at a pH value of 7 to 10, and also water-free products, preferably in the form of granules such as are obtained by conventional spray drying, drying in a thin-layer evaporator (flash dryer) or in a fluidized-bed dryer.

Hair treatment agents that are preferred as contemplated herein contain—based on the total weight of the agent—about 0.5 to about 20 wt %, preferably about 0.75 to about 15 wt %, further preferably about 1 to about 12 wt %, and, in particular, about 2 to about 10 wt % anionic surfactant(s) from the group of α-olefin sulfonates.

Hair treatment agents that are especially preferred as contemplated herein contain—based on the total weight of the agent—about 0.5 to about 20 wt %, preferably about 0.75 to about 15 wt %, further preferably about 1 to about 12 wt %, and, in particular, about 2 to about 10 wt % reaction products of $C_{12}$-$C_{18}$ olefins with sulfur trioxide composed essentially of alkene sulfonates and hydroxyalkane sulfonates.

In an exemplary embodiment, the hair treatment agents contain at least one anionic surfactant from the group of taurides.

Taurides—also known as N-acyl taurides, N-methyl-N-acyl taurates, N-acyl taurates, or N-acyl taurines—are a group of mildly anionic surfactants. The hydrophilic head group thereof is composed of N-methyl taurine (2-methyl-aminoethanesulfonic acid), the lipophilic residue being composed of a long-chain carboxylic acid (fatty acid) linked via an amide bond. Lauric acid ($C_{12}$), myristic acid ($C_{14}$), palmitic acid ($C_{16}$), and stearic acid ($C_{18}$) are used as fatty acids, but mainly oleic acid (C18:1) and coco fatty acid mixture ($C_8$-$C_{18}$).

The general structural formula for taurides is:

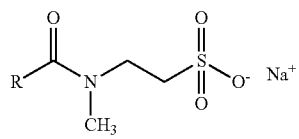

Preferred hair treatment agents as contemplated herein contain—based on the total weight of the agent—about 0.3 to about 10 wt %, preferably about 0.5 to about 8 wt %, further preferably about 0.6 to about 7 wt %, and, in particular, about 0.7 to about 5 wt % taurates of the formula (I)

where:
- $R^1$ is a linear or branched alkyl group having six to 30, preferably eight to 22 C atoms or a linear or branched monounsaturated or polyunsaturated alkenyl group having six to 30, preferably eight to 22 C atoms, and
- X is a counterion, preferably an alkali metal, alkaline earth metal, or ammonium ion.

Preferably, R in formula (I) denotes a cocoyl residue (coco fatty acid mixture $C_8$-$C_{18}$). Hair treatment agents that are especially preferred herein contain—based on the total weight of the agent—about 0.3 to about 10 wt %, preferably about 0.5 to about 8 wt %, further preferably about 0.6 to about 7 wt %, and, in particular, about 0.7 to about 5 wt % sodium methyl cocoyl taurate.

Corresponding surfactants are distributed under the tradenames of, for example, Adinol®, Geropon®, Hostapon®, Metaupon®, Nikkol®, Protapon®, Pureact®, and Tauranol®.

It has proven preferable to minimize the amount of sulfate surfactants in the hair treatment agents contemplated herein in order to make them even milder and more effective. Hair treatment agents that are preferred as contemplated herein are characterized by containing—based on the weight of the agent—less than about 1 wt %, preferably less than about 0.5 wt %, and, in particular, less than about 0.1 wt % sulfate surfactant(s).

In an exemplary embodiment, the hair treatment agents contemplated herein contain at least one amphoteric surfactant. Amphoteric surfactants or zwitterionic surfactants refer to surfactants that have both a negatively charged functional group and a positively charged functional group.

Particularly suitable zwitterionic surfactants are the so-called betaines, such as the N-alkyl-N,N-dimethylammonium glycinates, for example cocoalkyl dimethylammonium glycinate; the N-acylaminopropyl-N,N-dimethylammonium glycinates, for example cocoacylaminopropyl dimethylammonium glycinate; and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known by the INCI designation cocamidopropyl betaine.

Further examples of suitable ampholytic surfactants are N-alkylglycines, N-alkylaminopropionic acids, N-alkylaminobutyric acids, N-alkyliminodipropionic acids, N-hydroxyethyl-N-alkyl amidopropyl glycines, N-alkyl taurines, N-alkyl sarcosines, 2-alkylaminopropionic acids, and alkylaminoacetic acids having in each case about 8 to 24 C atoms in the alkyl group. Particularly preferred ampholytic surfactants are N-cocoalkyl aminopropionate, cocoacylaminoethyl aminopropionate, and $C_{12}$-$C_{18}$ acyl sarcosine.

Preferred hair treatment agents contemplated herein contain—based on the total weight of the agent—about 0.3 to about 10 wt %, preferably about 0.5 to about 8 wt %, further preferably about 0.75 to about 6 wt %, and, in particular, about 1 to about 5 wt % amphoteric surfactant(s).

Particularly preferred hair treatment agents contemplated herein are characterized by containing amphoteric surfactant(s) from the groups of the
- N-alkylglycines,
- N-alkylpropionic acids,
- N-alkylaminobutyric acids,
- N-alkyliminodipropionic acids,
- N-hydroxyethyl-N-alkylamidopropylglycines,
- N-alkyl taurines,
- N-alkyl sarcosines,
- 2-alkylaminopropionic acids having in each case about 8 to 24 C atoms in the alkyl group,
- alkylaminoacetic acids having in each case about 8 to 24 C atoms in the alkyl group,
- N-cocoalkyl aminopropionate,
- cocoacylaminoethyl aminopropionate,
- $C_{12}$-$C_{18}$ acyl sarcosine,
- N-alkyl-N,N-dimethylammonium glycinates, for example cocoalkyl dimethylammonium glycinate,
- N-acylaminopropyl-N,N-dimethylammonium glycinates, for example cocoacylaminopropyl dimethylammonium glycinate,
- 2-alkyl-3-carboxymethyl-3-hydroxyethyl imidazolines each having 8 to 18 C atoms in the alkyl or acyl group,
- cocoacylaminoethyl hydroxyethyl carboxymethyl glycinate,
- the compounds known by the INCI designation cocamidopropyl betaine, and
- the compounds known by the INCI designation disodium cocoamphodiacetate, wherein preferred agents contain the amphoteric surfactant(s) in quantities of about 0.3 to about 10 wt %, preferably about 0.5 to about 8 wt %, further preferably about 0.75 to about 6 wt %, and, in particular, about 1 to about 5 wt %, based in each case on the total agent.

Particularly preferred hair treatment agents contain, as amphoteric surfactants, betaines of formula (Bet-I):

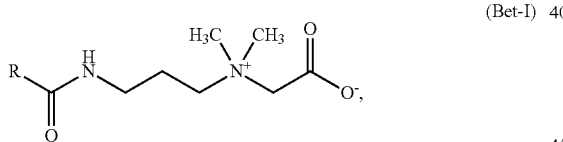
(Bet-I)

in which R denotes a straight-chain or branched, saturated or mono- or polyunsaturated alkyl or alkenyl residue having 8 to 24 carbon atoms.

These surfactants are referred to according to the INCI nomenclature as amidopropyl betaines, wherein the representatives derived from coconut fatty acids are preferred and referred to as cocamidopropyl betaines. It is particularly preferable as contemplated herein to use surfactants of the formula (Bet-I) that are a mixture of the following representatives:

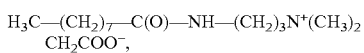

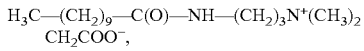

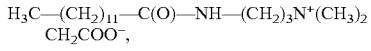

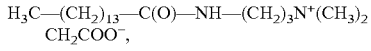

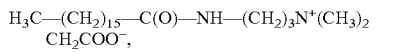

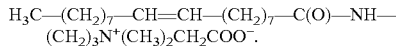

It is particularly preferable to use surfactants of the formula (Bet-I) within narrower quantity ranges. Preferred here are hair treatment agents as contemplated herein that—based on the total weight of the agent—contain about 0.25 to about 8 wt %, preferably about 0.5 to about 7 wt %, further preferably about 0.75 to about 6.5 wt %, and, in particular, about 1 to about 5.5 wt % surfactant(s) of the formula (Bet-I).

In addition to the ampho-surfactants of formula (Bet-1), or instead of them, the hair treatment agents contemplated herein may, with particular preference, contain as amphoteric surfactants betaines of formula (Bet-II):

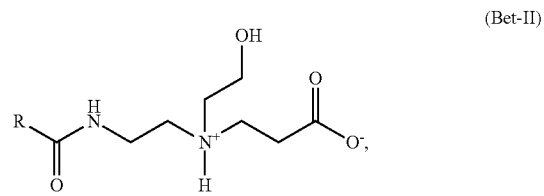
(Bet-II)

in which R denotes a straight-chain or branched, saturated or mono- or polyunsaturated alkyl or alkenyl residue having 8 to 24 carbon atoms.

These surfactants are referred to according to the INCI nomenclature as amphoacetates, wherein the representatives derived from coconut fatty acids are preferred and referred to as cocoamphoacetates.

For technical reasons relating to manufacture thereof, surfactants of this type always also contain betaines of formula (Bet-IIa):

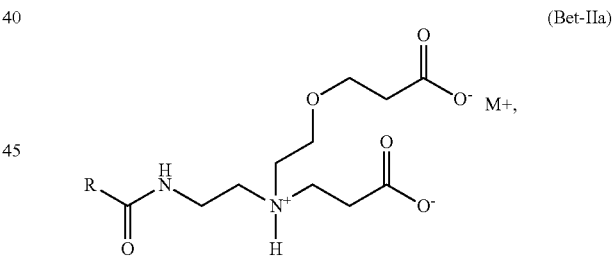
(Bet-IIa)

in which R denotes a straight-chain or branched, saturated or mono- or polyunsaturated alkyl or alkenyl residue having 8 to 24 carbon atoms, and M denotes a cation.

These surfactants are referred to according to the INCI nomenclature as amphodiacetates, wherein the representatives derived from coconut fatty acids are preferred and referred to as cocoamphodiacetates.

It is particularly preferable herein to use surfactants of the formula (Bet-III) that are a mixture of the following representatives:

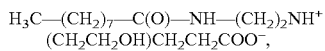

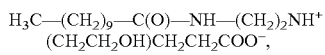

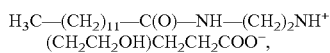

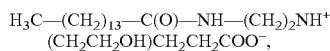
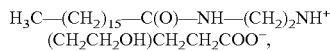
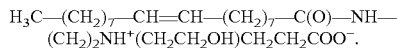

It is particularly preferable to use surfactants of the formula (Bet-III) within narrower quantity ranges. Preferred here are hair treatment agents contemplated herein that—based on the total weight of the agent—contain about 0.25 to about 8 wt %, preferably about 0.5 to about 7 wt %, further preferably about 0.75 to about 6.5 wt %, and, in particular, about 1 to about 5.5 wt % surfactant(s) of the formula (Bet-II).

In summary, preferred cosmetic agents as contemplated herein are those in which the residue R in the formulas (Bet-I) and (Bet-III) is selected from

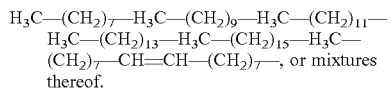

The hair treatment agents may additionally contain nonionic surfactants and/or cationic surfactant(s).

Examples of suitable nonionic surfactants include:
addition products of about 4 to about 30 mol of ethylene oxide and/or 0 to about 5 mol of propylene oxide to linear fatty alcohols having 8 to 22 C atoms, to fatty acids having 12 to 22 C atoms, and to alkylphenols having 8 to 15 C atoms in the alkyl group,
ethylene oxide and polyglycerol addition products to methyl glucoside fatty acid esters, fatty acid alkanolamides, and fatty acid glucamides,
$C_8$-$C_{30}$ fatty acid monoesters and diesters of addition products of 1 to 30 mol of ethylene oxide to glycerol,
amine oxides,
sorbitan fatty acid esters and addition products of ethylene oxide to sorbitan fatty acid esters, such as e.g. polysorbates,
fatty acid alkanolamides of the following general formula,

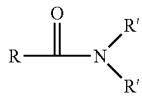

in which R preferably signifies a linear or branched saturated or unsaturated alkyl or alkenyl residue having 8 to 24 carbon atoms, and the residues R' denote hydrogen or the group —$(CH_2)_n$OH, in which n signifies the number 2 or 3, with the proviso that at least one of the residues R' denotes the aforementioned residue—$(CH_2)_n$OH.

sugar fatty acid esters and addition products of ethylene oxide to sugar fatty acid esters,
addition products of ethylene oxide to fatty acid alkanolamides and fatty amines, and/or
alkyl (oligo)glucosides,
mixtures of alkyl (oligo)glucosides and fatty alcohols, for example, the commercially available product Montanov® 68,
addition products of about 5 to about 60 mol of ethylene oxide to castor oil and hydrogenated castor oil,
partial esters of polyols having 3-6 carbon atoms with saturated fatty acids having 8 to 22 C atoms, sterols. Sterols are understood to refer to a group of steroids that bear a hydroxy group at the C atom 3 of the steroid structure, and are isolated both from animal tissue (zoosterols) and from vegetable fats (phytosterols). Examples of zoosterols include cholesterol and lanosterol. Examples of suitable phytosterols include ergosterol, stigmasterol, and sitosterol. There are also sterols that are isolated from fungi and yeasts (so-called mycosterols).

Phospholipids. These are understood to mean principally the glucose phospholipids, which are obtained e.g., as lecithins or phosphatidylcholines from for example, egg yolk or plant seeds (e.g., soybeans).

Suitable alkyl (oligo)glycosides can be selected from compounds of the general formula RO-[G]$_x$, in which [G] is preferably derived from aldoses and/or ketoses having 5-6 carbon atoms, preferably from glucose.

The index number x denotes the degree of oligomerization (DP), i.e. the distribution of mono- and oligoglycosides. The index number x preferably has a value in the range from about 1 to about 10, more preferably in the range from about 1 to about 3, wherein it need not be a whole number but can be a fraction which can be determined by analysis.

Particularly preferred alkyl (oligo)glycosides have a degree of oligomerization between about 1.2 and about 1.5.

The residue R preferably denotes at least one alkyl and/or alkenyl residue having 4 to 24 C atoms.

Especially preferred alkyl (oligo)glycosides are compounds that are known under the INCI designations Caprylyl/Capryl Glucoside, Decyl Glucoside, Lauryl Glucoside, and Coco Glucoside.

Suitable amine oxides may be selected from at least one compound of the general formulae (A-I) or (A-II)

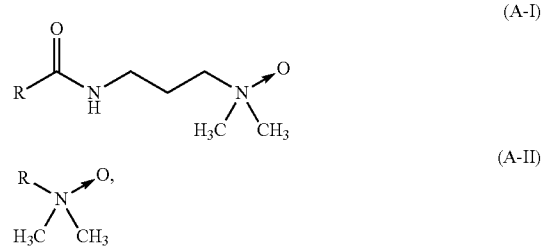

in which R in each case denotes a straight-chain or branched, saturated or mono- or polyunsaturated alkyl or alkenyl residue having 6 to 24 carbon atoms, preferably 8 to 18 carbon atoms.

The surfactants of the aforementioned formulae (A-I) or (A-III) that are known under the INCI designations Cocamine Oxide, Lauramine Oxide, and/or Cocamidopropylamine Oxide and are commercially available from a number of suppliers are preferred in particular.

Suitable $C_8$-$C_{30}$ fatty acid monoesters and diesters of addition products of about 1 to about 30 mol of ethylene oxide to glycerol are preferably understood to be those with the INCI designations PEG(1-10) Glyceryl Cocoate, in particular, PEG-7 Glyceryl Cocoate.

It may also be advantageous to combine the ethoxylated fatty acid esters with other ethoxylated fatty acid esters. Such product mixtures are commercially available, e.g., under the name "Antil 200®" " (INCI designation: PEG-200 Hydrogenated Glyceryl Palmate, PEG-7 Glyceryl Cocoate) from Evonik.

Particularly preferred nonionic surfactants that may be contained in the hair treatment agents contemplated herein are: fatty acid alkanolamides, in particular, compounds known by the INCI designations Cocamide MEA and/or Cocamide MIPA; alkyl (oligo)glucosides, in particular, compounds known by the INCI designations Caprylyl/Capryl Glucoside, Decyl Glucoside, Lauryl Glucoside and/or Coco Glucoside; $C_8$-$C_{30}$ fatty acid monoesters and diesters of addition products of 1 to 30 mol ethylene oxide to glycerol, in particular, the compound known by the INCI designations PEG-7 Glyceryl Cocoate; and/or addition products of 4 to 30 mol ethylene oxide and/or 0 to 5 mol propylene oxide to linear fatty alcohols having 8 to 22 C atoms.

Cocamide MEA and/or PEG-7 Glyceryl Cocoate are especially preferred in light of the foam-stabilizing and moisturizing properties thereof.

Also available for use herein are cationic surfactants of the following types: quaternary ammonium compounds, esterquats, and amidoamines. Preferred quaternary ammonium compounds are ammonium halides, in particular chlorides and bromides, such as alkyl trimethylammonium chlorides, dialkyl dimethylammonium chlorides, and trialkyl methylammonium chlorides. The long alkyl chains of these surfactants preferably have 10 to 18 carbon atoms, such as in, for example, cetyl trimethylammonium chloride, stearyl trimethylammonium chloride, distearyl dimethylammonium chloride, lauryl dimethylammonium chloride, lauryl dimethylbenzylammonium chloride, and tricetyl methylammonium chloride. The preferred cationic surfactants also include the imidazolium compounds known under the INCI designations quaternium-27 and quaternium-83.

Particularly preferred hair treatment agents as contemplated herein are characterized by containing, as a cationic conditioner, about 0.05 to about 7.5 wt %, preferably about 0.1 to about 5 wt %, particularly preferably about 0.2 to about 3.5 wt %, and, in particular, about 0.25 to about 2.5 wt % (based on the total weight of the agent) cationic surfactant(s) from the group of the quaternary ammonium compounds and/or the esterquats and/or the amidoamines, wherein (a) preferred cationic surfactant(s) is/are selected from
  alkyl trimethylammonium chlorides having preferably 10 to 18 carbon atoms in the alkyl residue and/or
  diallyl dimethylammonium chlorides having preferably 10 to 18 carbon atoms in the alkyl residue and/or
  trialkyl methylammonium chlorides having preferably 10 to 18 carbon atoms in the alkyl residue and/or
  cetyl trimethylammonium chloride and/or
  stearyl trimethylammonium chloride and/or
  distearyl dimethylammonium chloride and/or
  lauryl dimethylammonium chloride and/or
  lauryl dimethyl benzylammonium chloride and/or
  tricetyl methylammonium chloride
  Quatemium-27 and/or
  Quatemium-83 and/or
  N-methyl-N(2-hydroxyethyl)-N,N-(ditalgacyloxyethyl) ammonium methosulfate and/or
  N-methyl-N(2-hydroxyethyl)-N,N-(distearoyloxyethyl) ammonium methosulfate and/or
  N,N-dimethyl-N,N-distearoyloxyethyl ammonium chloride and/or
  N,N-di-(2-hydroxyethyl)-N,N-(fatty acid ester ethyl)ammonium chloride.

In an exemplary embodiment, the hair treatment agents contain at least one silver salt selected from silver acetate, silver adipate, silver citrate, silver galactarate, silver gluconate, silver lactate, silver malate, silver mandelate, silver salicylate, silver succinate, silver sulfate, and silver tartrate, or mixtures thereof.

Irrespective of which silver salt(s) is/are contained in the agents as contemplated herein, preferred hair treatment agents are those containing—based on the weight of the agent—about 0.01 to about 2 wt %, preferably about 0.01 to about 1 wt %, further preferably about 0.025 to about 0.25 wt %, and, in particular, about 0.05 to about 0.3 wt % silver salt(s).

Especially preferably, the amount of silver salt(s) is selected so that the compositions as contemplated herein have a defined content of silver ions. Preferred here are hair treatment agents that contain silver ions in a total amount of about 1 to about 100 ppm, preferably about 2 to about 50 ppm, especially preferably about 5 to about 20 ppm, exceptionally preferably about 7 to about 10 ppm, based in each case on the weight of the hair treatment agent.

The hair treatment agents contain at least one organic acid selected from adipic acid, succinic acid, citric acid, acetic acid, galactaric acid, gluconic acid, malic acid, mandelic acid, lactic acid, salicylic acid, sulfuric acid, and tartaric acid. Irrespective of which acid(s) is/are contained in the agents contemplated herein, preferred hair treatment agents are those containing—based on the weight of the agent—about 0.01 to about 3 wt %, preferably about 0.01 to about 2 wt %, further preferably about 0.025 to about 1.5 wt %, and, in particular, about 0.05 to about 1 wt % organic acid(s) from the group of adipic acid, succinic acid, citric acid, acetic acid, galactaric acid, gluconic acid, malic acid, mandelic acid, lactic acid, salicylic acid, sulfuric acid, and tartaric acid.

It is exceptionally preferred if the acid contained in the agents and the silver salt contained in the agents are matched to one another, i.e., the silver salt is adjusted to the respective acid being used.

Agents that are especially preferred herein accordingly contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver acetate, and about 0.01 to about 3 wt %, preferably about 0.01 to about 2 wt %, further preferably about 0.025 to about 1.5 wt % and, in particular, about 0.05 to about 1 wt % acetic acid.

Further agents that are especially preferred contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver adipate, and about 0.01 to about 3 wt %, preferably about 0.01 to about 2 wt %, further preferably about 0.025 to about 1.5 wt % and, in particular, about 0.05 to about 1 wt % adipic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver citrate, and about 0.01 to about 3 wt %, preferably about 0.01 to about 2 wt %, further preferably about 0.025 to about 1.5 wt % and, in particular, about 0.05 to about 1 wt % citric acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver galactarate, and about 0.01 to about 3 wt %, preferably about 0.01 to about 2 wt %, further preferably about 0.025 to about 1.5 wt % and, in particular, about 0.05 to about 1 wt % galactaric acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver gluconate, silver lactate, silver malate, silver mandelate, silver salicylate, silver succinate, silver sulfate, silver tartrate and about 0.01 to about 3 wt %, preferably about 0.01 to about 2 wt %, further preferably about 0.025 to about 1.5 wt %, and, in particular, about 0.05 to about 1 wt % succinic acid, gluconic acid, malic acid, mandelic acid, lactic acid, salicylic acid, sulfuric acid, tartaric acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver gluconate, and about 0.01 to about 3 wt %, preferably about 0.01 to about 2 wt %, further preferably about 0.025 to about 1.5 wt % and, in particular, about 0.05 to about 1 wt % gluconic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver lactate, and about 0.01 to about 3 wt %, preferably about 0.01 to about 2 wt %, further preferably about 0.025 to about 1.5 wt % and, in particular, about 0.05 to about 1 wt % lactic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver malate, and about 0.01 to about 3 wt %, preferably about 0.01 to about 2 wt %, further preferably about 0.025 to about 1.5 wt % and, in particular, about 0.05 to about 1 wt % malic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver mandelate, and about 0.01 to about 3 wt %, preferably about 0.01 to about 2 wt %, further preferably about 0.025 to about 1.5 wt % and, in particular, about 0.05 to about 1 wt % mandelic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver salicylate, and about 0.01 to about 3 wt %, preferably about 0.01 to about 2 wt %, further preferably about 0.025 to about 1.5 wt % and, in particular, about 0.05 to about 1 wt % salicylic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver succinate, and about 0.01 to about 3 wt %, preferably about 0.01 to about 2 wt %, further preferably about 0.025 to about 1.5 wt % and, in particular, about 0.05 to about 1 wt % succinic acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver sulfate, and about 0.01 to about 3 wt %, preferably about 0.01 to about 2 wt %, further preferably about 0.025 to about 1.5 wt % and, in particular, about 0.05 to about 1 wt % sulfuric acid.

Further agents that are especially preferred herein contain—based on the weight of the agent—about 0.01 to about 2 wt %, preferably about 0.01 to about 1 wt %, further preferably about 0.025 to about 0.25 wt %, and, in particular, about 0.05 to about 0.3 wt % silver tartrate, and about 0.01 to about 3 wt %, preferably about 0.01 to about 2 wt %, further preferably about 0.025 to about 1.5 wt % and, in particular, about 0.05 to about 1 wt % tartaric acid.

It has proven especially advantageous to use the two ingredients-silver salt and corresponding acid-preassembled in the form of a complex. Such complexes can be prepared with suitable passivating agents into a separate and storage-stable raw material and can then be stably added in, even in highly aqueous systems.

In an exemplary embodiment, preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver lactate/lactic acid complexes of the form

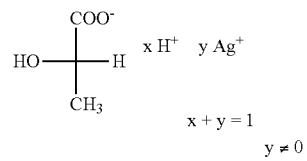

or the form

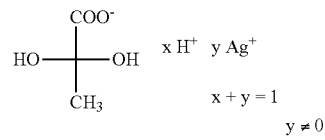

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver acetate/acetic acid complexes of the form

x+y=1
y≠0 with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver sulfate/sulfuric acid complexes of the form

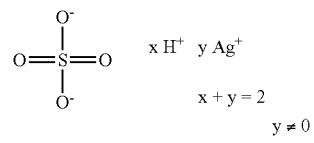

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver malate/malic acid complexes of the form

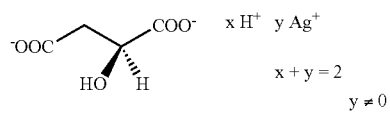

or the form

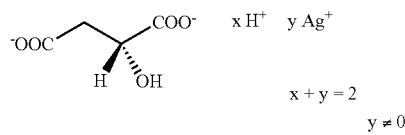

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver succinate/succinic acid complexes of the form

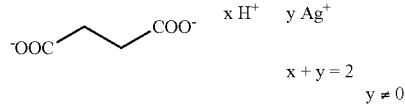

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver tartrate/tartaric acid complexes of the form

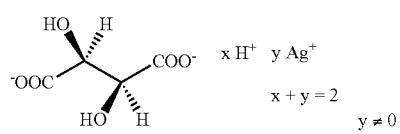

or the form

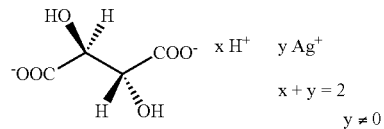

or the form

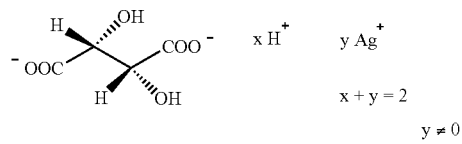

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver mandelate/mandelic acid complexes of the form

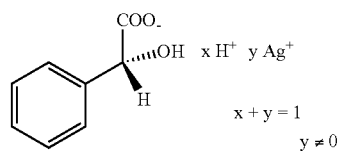

or the form

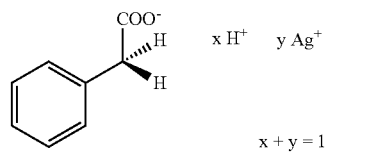

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver salicylate/salicylic acid complexes of the form

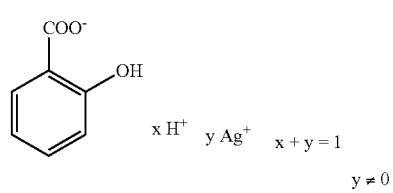

with a moisture content of up to about 90 wt %, based on the total mass of the complex, in combination with one or more passivating agents selected from the group of phyllosilicates and/or talc.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver gluconate/gluconic acid complexes of the form

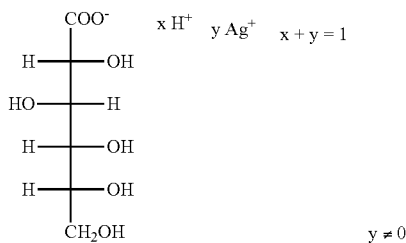

with a moisture content of up to about 90 wt %, based on the total mass of the complex, in combination with one or more passivating agents selected from the group of phyllosilicates and/or talc.

Especially preferred hair treatment agents as contemplated herein contain—based on the total weight of the agent—about 0.01 to about 2 wt %, preferably about 0.01 to about 1 wt %, further preferably about 0.025 to about 0.25 wt %, and, in particular, about 0.05 to about 0.3 wt % silver citrate/citric acid complexes of the form

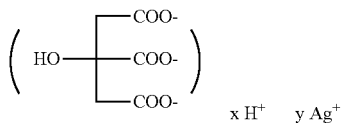

where x+y=3 and y≠0
with a moisture content of up to about 90 wt %, based on the total mass of the complex, in combination with one or more passivating agents selected from the group of silicic acids.

Further preferred hair treatment agents as contemplated herein contain—based on the total weight of the agent—about 0.01 to about 5 wt %, preferably about 0.01 to about 3 wt %, further preferably about 0.025 to about 1.5 wt %, and, in particular, about 0.05 to about 1 wt % silver galactarate/galactaric acid complexes of the form

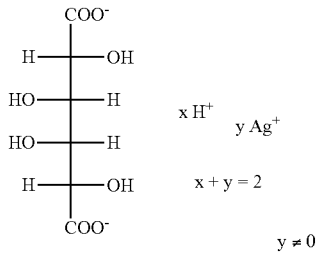

with a moisture content of up to about 90 wt %, based on the total mass of the complex, in combination with one or more passivating agents selected from the group of phyllosilicates and/or talc.

The hair treatment agents preferably contain the aforementioned substances in a cosmetically acceptable carrier. As contemplated herein, this preferably is understood to be an aqueous or aqueous-alcoholic carrier.

The cosmetic carrier preferably contains at least about 50 wt %, more preferably at least about 60 wt %, especially preferably at least about 70%, and particularly preferably at least about 75 wt % water.

The cosmetic carrier may also contain about 0.01 to about 40 wt %, preferably about 0.05 to about 30 wt %, and, in particular, about 0.1 to about 20 wt % at least one alcohol.

Suitable alcohols are, for example, ethanol, ethyl diglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1-hexanol, 2-hexanol, 1,2-hexanediol, 1,6-hexanediol, polyethylene glycolene, sorbitol, sorbitan, benzyl alcohol, or mixtures of these alcohols.

Water-soluble alcohols are especially preferred. Ethanol, 1,2-propylene glycol, glycerol, benzyl alcohol, and mixtures of these alcohols are particularly preferred.

For the hair treatment agents contemplated herein to have very favorable (scalp) skin compatibility, it is advantageous for the agents to have a slightly acidic pH value.

It has been discovered that the agents contemplated herein have an especially favorable skin compatibility and mildness in a pH range of about 4.2 to about 5.8.

In a first preferred embodiment, the hair treatment agents contemplated herein therefore preferably have a pH value in the range of about 4.2 to about 5.8, more preferably about 4.25 to about 5.6, especially preferably about 4.3 to about 5.5, extremely preferably about 4.35 to about 5.4, and particularly preferably about 4.4 to about 5.3.

The agents as contemplated herein may contain (a) cationic polymer(s).

Irrespective of which cationic polymer(s) is/are used, preferred hair treatment agents contain, based on the total weight of the agent, about 0.01 to about 3 wt %, preferably about 0.05 to about 2 wt %, further preferably about 0.1 to about 1.5 wt %, and, in particular, about 0.15 to about 0.8 wt % cationic polymer(s).

Cationic polymers that can preferably be used herein are described below:

Homopolymers of the general formula (G1-I),

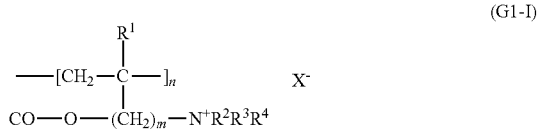

(G1-I)

in which $R^1$ is =—H or —$CH_3$, and $R^2$, $R^3$, and $R^4$ independently of each other are selected from $C_{1-4}$ alkyl, alkenyl, or hydroxyalkyl groups, m=1, 2, 3 or 4, n is a natural number and $X^-$ is a physiologically acceptable organic or inorganic anion, and copolymers consisting essentially of the monomer units listed in formula (G1-I), and non-ionogenic monomer units, are particularly preferred cationic polymers. Within the framework of these polymers, those for which at least one of the following conditions applies are preferred herein:

$R^1$ denotes a methyl group
$R^2$, $R^3$, and $R^4$ denote methyl groups
m has the value 2.

Appropriate physiologically acceptable counterions $X^-$ are, for example, halide ions, sulfate ions, phosphate ions, methosulfate ions, and organic ions such as lactate, citrate, tartrate, and acetate ions. Halide ions, in particular chloride, are preferred.

A particularly suitable homopolymer is the poly(methacryloxyethyltrimethylammonium) chloride (crosslinked, if desired) having the INCI name Polyquaternium-37. Such products are commercially available, for example, under the designations Rheocare® CTH (Cosmetic Rheologies) and Synthalen® CR (Ethnichem). The crosslinking may be accomplished, if desired, with the aid of olefinically polyunsaturated compounds, for example divinylbenzene, tetraallyloxyethane, methylene bisacrylamide, diallyl ether, polyallylpolyglyceryl ether, or allyl ethers of sugars or sugar derivatives such as erythritol, pentaerythritol, arabitol, mannitol, sorbitol, sucrose, or glucose. Methylene bisacrylamide is a preferred crosslinking agent.

The homopolymer is preferably used in the form of a non-aqueous polymer dispersion that should comprise a polymer proportion not less than about 30 wt %. Such polymer dispersions are obtainable commercially under the designations Salcare® SC 95 polymer dispersion (approx. 50% polymer proportion, further components: mineral oil (INCI designation: Mineral Oil) and tridecylpolyoxypropylenepolyoxyethylene ether (INCI designation: P PG-1-Trideceth-6)), and Salcare® SC 96 (approx. 50% polymer proportion, further components: mixture of diesters of propylene glycol with a mixture of caprylic and capric acid (INCI designation: Propylene Glycol Dicaprylate/Dicaprate) and tridecylpolyoxypropylenepolyoxyethylene ether (INCI designation: PPG-1-Trideceth-6)).

Copolymers having monomer units according to formula (G1-I) preferably contain acrylamide, methacrylamide, acrylic acid $C_{1-4}$ alkyl esters, and methacrylic acid $C_{1-4}$ alkyl esters as non-ionogenic monomer units. Among these non-ionogenic monomers, acrylamide is particularly preferred. As in the case of the homopolymers described above, these copolymers may also be crosslinked. A copolymer preferred herein is the crosslinked acrylamide-methacryloyloxyethyltrimethylammonium chloride copolymer. Such copolymers, in which the monomers are present at a weight ratio of approximately 20:80, are obtainable commercially as an approximately 50% non-aqueous polymer dispersion under the name Salcare® SC 92.

Further preferred cationic polymers are, for example,
quaternized cellulose derivatives such as those commercially obtainable under the designations Celquat® and Polymer JR®. The compounds Celquat® H 100, Celquat® L 200, and Polymer JR® 400 are preferred quaternized cellulose derivatives,
cationic alkylpolyglycosides,
cationized honey, for example the commercial product Honeyquat® 50,
cationic guar derivatives, such as in particular the products marketed under the trade names Cosmedia® Guar and Jaguar®,
polymeric dimethyldiallylammonium salts and copolymers thereof with esters and amides of acrylic acid and methacrylic acid. The products obtainable commercially under the designations Merquat® 100 (poly (dimethyldiallylammonium chloride)) and Merquat® 550 (dimethyldiallylammonium chloride/acrylamide copolymer) are examples of such cationic polymers,
Copolymers of vinylpyrrolidone with quaternized derivatives of dialkylaminoalkyl acrylate and methacrylate, such as with diethylsulfate quaternized vinylpyrrolidone-dimethylaminoethyl methacrylate copolymers. Such compounds are commercially available under the designations Gafquat®734 and Gafquat®755,
Vinylpyrrolidone-vinylimidazolium methochloride copolymers, such as offered under the designations Luviquat® FC 370, FC 550, FC 905, and HM 552,
quaternized poly(vinylalcohol),
and the polymers known under the names Polyquaternium-2, Polyquaternium-17, Polyquaternium-18, and Polyquaternium-27, having quaternary nitrogen atoms in the main polymer chain.

The polymers known under the designations Polyquaternium-24 (commercial product, e.g. Quatrisoft® LM 200) may also be used as cationic polymers. It is also possible, as contemplated herein, to use the copolymers of vinylpyrrolidone, such as are available as commercial products Copolymer 845 (manufacturer: ISP), Gaffix® VC 713 (manufacturer: ISP), Gafquat® ASCP 1011, Gafquat® HS 110, Luviquat® 8155, and Luviquat® MS 370.

Cationic protein hydrolysates may also be used as cationic polymers, wherein preferred agents contain one or more cationic protein hydrolysates from the group Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, and Quaternium-79 Hydrolyzed Wheat Protein.

It is especially preferable as contemplated herein to use cationic polysaccharide polymers as the cationic polymers.

Cationic polysaccharide polymers increase the nourishing performance of the hair treatment agents contemplated herein (in particular, the effectiveness of the agents against hair breakage). Suitable cationic polysaccharide polymers may be selected from cationic cellulose compounds and/or cationic guar derivatives.

Especially preferred hair treatment agents contemplated herein contain, as cationic polysaccharide polymer(s), about 0.01 to about 3 wt %, preferably about 0.05 to about 2 wt %, further preferably about 0.1 to about 1.5 wt %, and, in particular, about 0.15 to about 0.8 wt % at least one polymer from the group of cationic cellulose polymers and/or cationic guar derivatives, based on the total weight of the agent.

Cationic cellulose compounds as contemplated herein are those that bear more than one permanent cationic charge in at least one side chain. Cellulose is composed of beta-1,4-glycosidically linked D-glucopyranose units, and forms unbranched, water-insoluble chains. The side chain of a cellulose is defined as chemical substituents that bond to the cellulose backbone and which are not found in native cellulose, because they have been subsequently introduced e.g. by chemical synthesis.

It is preferred to use quaternized cellulose polymers derived from hydroxy ($C_2$-$C_4$) alkyl celluloses, especially preferably from hydroxyethyl celluloses.

Such polymers are known to a person skilled in the art and commercially available from different companies. The cationic cellulose derivatives known under the INCI designations Polyquaternium-4, Polyquaternium-10, Polyquaternium-24, Polyquaternium-67 and/or Polyquaternium-72 are especially preferred. Polyquaternium-10, Polyquaternium-24 and/or Polyquaternium-67 are particularly preferred, especially Polyquaternium-10.

Preferred hair treatment agents as contemplated herein contain, as cationic polysaccharide polymer(s), about 0.01 to about 3 wt %, preferably about 0.05 to about 2 wt %, further preferably about 0.1 to about 1.5 wt %, and, in particular, about 0.15 to about 0.8 wt % at least one polymer from the group of Polyquaternium-4, Polyquaternium-10, Polyquaternium-24, Polyquaternium-67 and/or Polyquaternium-72

Especially preferred hair treatment agents contemplated herein contain, based on the total weight of the agent, about 0.01 to about 3 wt %, preferably about 0.05 to about 2 wt %, further preferably about 0.1 to about 1.5 wt %, and, in particular, about 0.15 to about 0.8 wt % Polyquaternium-10 as the cationic polysaccharide(s).

Suitable cationic guar derivatives as contemplated herein are cationic hydroxyalkyl guar derivatives, preferably cationic hydroxyethyl trimethylammonium guar and/or cationic hydroxypropyl trimethylammonium guar having a mean molecular weight between about 100,000 and about 2,000,000 daltons. Particularly preferred are the cationic guar polymers that are known under the INCI designation Guar Hydroxypropyltrimonium Chloride and have a molecular weight (weight-average) between about 200,000 and about 1,600,000 daltons. The cationic charge density of these guar polymers is preferably at least about 0.4 meq/g, preferably at least about 0.5 meq/g, and, in particular, at least about 0.6 meq/g. The nitrogen content thereof is preferably in the range of about 1.1 to about 1.8 wt % (based on the total weight thereof).

Cationic guar derivatives known under the INCI designation Guar Hydroxypropyltrimonium Chloride are known to a person skilled in the art and are available, for example, under the trade names Cosmedia® Guar, N-Hance®, and/or Jaguar® from a variety of providers.

Especially preferred hair treatment agents contemplated herein contain, based on the total weight of the agent, about 0.01 to about 3 wt %, preferably about 0.05 to about 2 wt %, further preferably about 0.1 to about 1.5 wt %, and, in particular, about 0.15 to about 0.8 wt % Guar Hydroxypropyltrimonium as the cationic polysaccharide(s).

The hair treatment agents as contemplated herein may contain vegetable oils, vegetable butters, and/or waxes. These vegetable oil components endow the hair with an improved combability and manageability, and increase hair shine.

Suitable vegetable oil components include natural (vegetable) oils and/or butters that typically contain triglycerides and mixtures of triglycerides.

Preferred natural oils are coconut oil, (sweet) almond oil, walnut oil, peach kernel oil, apricot kernel oil, argan oil, avocado oil, tea tree oil, soybean oil, sesame oil, sunflower oil, *Camellia japonica* oil, evening primrose oil, rice bran oil, palm kernel oil, mango kernel oil, marula oil, meadowfoam seed oil, safflower oil, macadamia nut oil, grape seed oil, amaranth seed oil, bamboo oil, olive oil, wheat germ oil, pumpkin seed oil, mallow oil, hazelnut oil, safflower oil, canola oil, sasanqua oil, jojoba oil, rambutan oil, cocoa butter, and/or shea butter.

Beeswax and/or candelilla wax may preferably be used as suitable natural or vegetable waxes.

Particularly preferred vegetable oil components are (sweet) almond oil, peach kernel oil, apricot kernel oil, amaranth seed oil, argan oil, olive oil, jojoba oil, cocoa butter, and/or shea butter.

Apricot kernel oil, argan oil, olive oil, and/or jojoba oil are especially preferable.

In a preferred embodiment, the hair treatment agents as contemplated herein preferably contain coconut oil, (sweet) almond oil, walnut oil, peach kernel oil, apricot kernel oil, argan oil, avocado oil, tea tree oil, soybean oil, sesame oil, sunflower oil, *Camellia japonica* oil, evening primrose oil, rice bran oil, palm kernel oil, mango kernel oil, marula oil, meadowfoam seed oil, safflower oil, macadamia nut oil, grape seed oil, amaranth seed oil, bamboo oil, olive oil, wheat germ oil, pumpkin seed oil, mallow oil, hazelnut oil, safflower oil, canola oil, sasanqua oil, jojoba oil, rambutan oil, cocoa butter, and/or shea butter.

Within this embodiment, it is especially preferred if the hair treatment agents contain (sweet) almond oil, peach kernel oil, apricot kernel oil, amaranth seed oil, argan oil, olive oil, jojoba oil, cocoa butter, and/or shea butter.

The proportion by weight of the at least one vegetable oil, vegetable butter, and/or vegetable wax to the total weight of the hair treatment agents contemplated herein is preferably about 0.02 to about 2.50 wt %, more preferably about 0.03 to about 2.00 wt %, further preferably about 0.04 to about 1.50 wt %, and, in particular, about 0.05 to about 1.00 wt %.

In addition to the aforementioned essential and optional components, the hair treatment agents contemplated herein may, in another preferred embodiment for further increasing the nourishing properties of the agents, contain at least one additional hair-conditioning ingredient, which may be selected from the group of
protein hydrolysates,
vitamins,
plant extracts, and/or
glycerol.

Suitable protein hydrolysates are understood to be product mixtures that can be obtained by acidically, basically, or enzymatically catalyzed breakdown of proteins.

Protein hydrolysates of plant, animal, and/or marine origin can be used.

Animal protein hydrolysates are, for example, elastin, collagen, keratin, silk, and milk protein hydrolysates, which can also be present in the form of salts. Such products are sold for example under the trademarks Dehylan® (Cognis), Promois® (Interorgana), Collapuron® (Cognis), Nutrilan®

(Cognis), Gelita-Sol® (Deutsche Gelatine Fabriken Stoess & Co), Lexein® (Inolex), and Kerasol® (Croda).

Protein hydrolysates of plant origin, for example soy, almond, rice, pea, potato, and wheat protein hydrolysates, are preferred. Such products are available, for example, under the trademarks Gluadin® (Cognis), DiaMin® (Diamalt), Lexein® (Inolex), and Crotein® (Croda). Cationized protein hydrolysates can also be used, wherein the underlying protein hydrolysate can derive from: animal sources, for example from collagen, milk, or keratin; from plant sources, for example from wheat, maize, rice, potatoes, soy, or almonds; from marine life forms, for example from fish collagen or algae; or from protein hydrolysates obtained by biotechnology. The protein hydrolysates underlying the cationic derivatives can be obtained from the corresponding proteins by means of a chemical, in particular alkaline or acid hydrolysis, an enzymatic hydrolysis, and/or a combination of both types of hydrolysis. The hydrolysis of proteins generally gives rise to a protein hydrolysate having a molecular weight distribution from approximately 100 daltons to up to several thousand daltons. Preferred cationic protein hydrolysates are those having an underlying protein component that has a molecular weight of about 100 to up to about 25,000 daltons, preferably about 250 to about 5000 daltons. Cationic protein hydrolysates are moreover understood to include quaternized amino acids and mixtures thereof. The quaternization of the protein hydrolysates or the amino acids is frequently performed using quaternary ammonium salts such as for example N,N-dimethyl-N-(n-alkyl)-N-(2-hydroxy-3-chloro-n-propyl) ammonium halides. The cationic protein hydrolysates can moreover also be further derivatized. Typical examples of the cationic protein hydrolysates and derivatives are the commercially available products known under the following INCI designations: Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

The proportion by weight of the protein hydrolysate(s) to the total weight of the hair treatment agents is preferably about 0.01 to about 5 wt %, preferably about 0.025 to about 3 wt %, and, in particular about 0.05 to about 2 wt %.

Regardless of the source (plant, animal, marine, etc.), protein hydrolysates contain individual amino acids, oligopeptides, and optionally polypeptides, depending on the degree of hydrolysis.

Particularly preferably, the hair treatment agents contemplated herein contain at least one oligopeptide that comprises at least one amino acid sequence Glu-Glu-Glu, wherein the amino group may be present in free or protonated form and the carboxy groups may be present in free or deprotonated form.

Particularly preferred hair treatment agents as contemplated herein characterized by containing—based on the total weight of the agent—about 0.0001 to about 10 wt % at least one oligopeptide that comprises at least one amino acid sequence Glu-Glu-Glu, wherein the amino group may be present in free or protonated form and the carboxy groups may be present in free or deprotonated form.

In this, as in all of the formulae below, the bracketed hydrogen atom of the amino group, like the bracketed hydroxy group of the acid function, means that the groups concerned may be present as such (in which case it is an oligopeptide with the respective number of amino acids as illustrated (in formula 3 above)) or that the amino acid sequence is present in an oligopeptide which also comprises other amino acids-depending on where the other amino acid(s) is/are bound, the bracketed components in the above formula are replaced by the other amino acid residue(s).

These preferred hair treatment agents as contemplated herein contain, based on the total weight of the agent, about 0.0001 to about 10 wt % at least one oligopeptide that comprises at least one amino acid sequence Glu-Glu-Glu, i.e., at least three consecutive glutamic acids.

Oligopeptides as contemplated herein are condensation products of amino acids linked by peptide bonds in the manner of an acid amide, comprising at least three and no more than 25 amino acids.

In preferred hair treatment agents contemplated herein, the oligopeptide comprises five to 15 amino acids, preferably six to 13 amino acids, particularly preferably seven to 12 amino acids, and, in particular, eight, nine, or 10 amino acids.

Depending on whether other amino acids are bound to the sequence Glu-Glu-Glu and on the nature of these amino acids, the molar mass of the oligopeptide contained in the agents contemplated herein may vary. Preferred hair treatment agents are characterized in that the oligopeptide has a molar mass of 650 to 3000 Da, preferably 750 to 2500 Da, particularly preferably 850 to 2000 Da, and, in particular, 1000 to 1600 Da.

In summary, preferred hair treatment agents are characterized in that the oligopeptide comprises 5 to 15 amino acids, preferably 6 to 13 amino acids, especially preferably 7 to 12 amino acids, and, in particular, eight, nine, or 10 amino acids, and has a molar mass of about 650 to about 3000 Da, preferably about 750 to about 2500 Da, especially preferably about 850 to about 2000, and, in particular, about 1000 to about 1600 Da.

As evidenced by the preferred number of amino acids in the oligopeptides and the preferred molar mass range, it is preferable to use oligopeptides that are composed not solely of the three glutamic acids, but also of other amino acids bonded to this sequence. These other amino acids are preferably selected from certain amino acids, whereas certain other representatives are less preferred.

Thus, it is preferable for the oligopeptides used in the agents contemplated herein to not contain methionine.

It is further preferable for the oligopeptides used in the agents contemplated herein to not contain cysteine and/or cystine.

It is further preferable for the oligopeptides used in the agents contemplated herein to not contain aspartic acid and/or asparagine.

It is further preferable for the oligopeptides used in the agents contemplated herein to not contain serine or threonine.

On the other hand, it is preferable for the oligopeptides used in the agents contemplated herein to contain tyrosine.

It is further preferable for the oligopeptides used in the agents contemplated herein to contain leucine.

It is further preferable for the oligopeptides used in the agents contemplated herein to contain isoleucine.

It is further preferable for the oligopeptides used in the agents contemplated herein to contain arginine.

It is further preferable for the oligopeptides used in the agents contemplated herein to contain valine.

Especially preferred oligopeptides or amino acid sequences contained in the preferred oligopeptides are described below:

A particularly preferred oligopeptide additionally contains tyrosine, which is preferably bound by the acid function thereof to the Glu-Glu-Glu sequence. Preferred hair treatment agents contemplated herein are therefore characterized in that the oligopeptide contained therein comprises at least one amino acid sequence Tyr-Glu-Glu-Glu, wherein the amino group may be present in free or protonated form and the carboxy groups may be present in free or deprotonated form.

Another particularly preferred oligopeptide additionally contains isoleucine, which is preferably bound by the amino function thereof to the Glu-Glu-Glu sequence. Preferred hair treatment agents contemplated herein are therefore characterized in that the oligopeptide contained therein comprises at least one amino acid sequence Glu-Glu-Glu-Ile, wherein the amino group may be present in free or protonated form and the carboxy groups may be present in free or deprotonated form.

Oligopeptides comprising both of the above-mentioned amino acids (tyrosine and isoleucine) are preferred. Particularly preferred hair treatment agents contemplated herein are then those in which the oligopeptide contained in the hair treatment agent comprises at least one amino acid sequence Tyr-Glu-Glu-Glu-Ile, wherein the amino group may be present in free or protonated form and the carboxy groups may be present in free or deprotonated form.

More preferred oligopeptides additionally contain arginine, which is preferably present bound to isoleucine. Particularly preferred hair treatment agents contemplated herein are then those in which the oligopeptide contained in the hair treatment agent comprises at least one amino acid sequence Tyr-Glu-Glu-Glu-Ile-Arg, wherein the amino group may be present in free or protonated form and the carboxy groups may be present in free or deprotonated form.

Even more preferred oligopeptides additionally contain valine, which is preferably present bound to the arginine. Further preferred hair treatment agents contemplated herein are therefore characterized in that the oligopeptide contained in the hair treatment agent comprises at least one amino acid sequence Tyr-Glu-Glu-Glu-Ile-Arg-Val, wherein the amino groups may be present in free or protonated form and the carboxy groups may be present in free or deprotonated form.

Even more preferred oligopeptides additionally contain leucine, which is preferably present bound to the valine. Further preferred hair treatment agents contemplated herein are therefore characterized in that the oligopeptide contained in the hair treatment agent comprises at least one amino acid sequence Tyr-Glu-Glu-Glu-Ile-Arg-Val-Leu, wherein the amino groups may be present in free or protonated form and the carboxy groups may be present in free or deprotonated form.

Especially preferred oligopeptides additionally contain leucine, which is preferably present bound to the tyrosine. Further preferred hair treatment agents contemplated herein are therefore characterized in that the oligopeptide contained in the hair treatment agent comprises at least one amino acid sequence Leu-Tyr-Glu-Glu-Glu-Ile-Arg-Val-Leu, wherein the amino groups may be present in free or protonated form and the carboxy groups may be present in free or deprotonated form.

Very especially preferably agents contemplated herein contain at least two oligopeptides that meet the aforementioned criteria but are different from one another. Thus, for example, it is preferable to use hair treatment agents that contain at least two mutually different oligopeptides A and B, which both contain the amino acid sequence Glu-Glu-Glu.

Such mutually different oligopeptides A and B are equivalent in bearing three consecutive Glu amino acids in the amino acid sequence thereof, but differ in the amino acids that are bound in front or behind. Mutually different peptides having a partial correspondence, which may be greater than in the three amino acids mentioned above, are preferred.

Thus, further preferred hair treatment agents are characterized in that at least two mutually different oligopeptides A and B both containing the amino acid sequence Glu-Glu-Glu-Ile are contained in the hair treatment agent.

Also preferred are hair treatment agents that contain at least two mutually different oligopeptides A and B that both contain the amino acid sequence Tyr-Glu-Glu-Glu.

Still further preferred hair treatment agents are characterized by containing at least two mutually different oligopeptides A and B both containing the amino acid sequence Glu-Glu-Glu-Ile-Arg.

Also, still further preferred hair treatment agents are characterized in that the hair treatment agent contains at least two mutually different oligopeptides A and B both containing the amino acid sequence Tyr-Glu-Glu-Glu-Ile.

Preferred hair treatment agents contemplated herein are therefore characterized in that the oligopeptide comprises at least one amino acid sequence Tyr-Glu-Glu-Glu-Ile, wherein the amino group may be present in free or protonated form and the carboxy groups may be present in free or deprotonated form.

Especially preferred hair treatment agents are characterized in that the hair treatment agent contains at least two mutually different oligopeptides A and B both containing the amino acid sequence Glu-Glu-Glu-Ile-Arg.

Also, especially preferred hair treatment agents are characterized in that the hair treatment agent contains at least two mutually different oligopeptides A and B both containing the amino acid sequence Tyr-Glu-Glu-Glu-Ile-Arg.

The oligopeptides preferably have an even greater structural correspondence. Thus, hair treatment agents that contain at least two mutually different oligopeptides A and B both containing the amino acid sequence Glu-Glu-Glu-Ile-Arg-Val are other preferred embodiments.

Also preferred embodiments are hair treatment agents that contain at least two mutually different oligopeptides A and B that both contain the amino acid sequence Tyr-Glu-Glu-Glu-Ile-Arg-Val.

Still further preferred hair treatment agents contemplated herein are characterized by containing at least two mutually different oligopeptides A and B both containing the amino acid sequence Glu-Glu-Glu-Ile-Arg-Val-Leu.

Also, still further preferred hair treatment agents contemplated herein are characterized by containing at least two mutually different oligopeptides A and B both containing the amino acid sequence Tyr-Glu-Glu-Glu-Ile-Arg-Val-Leu.

Preferred hair treatment agents as contemplated herein are therefore characterized in that the oligopeptide comprises at least one amino acid sequence Tyr-Glu-Glu-Glu-Ile-Arg-Val-Leu, wherein the amino group may be present in free or protonated form and the carboxy groups may be present in free or deprotonated form.

Especially preferred hair treatment agents contemplated herein are characterized by containing at least two mutually different oligopeptides A and B, wherein the oligopeptide A comprises the amino acid sequence Leu-Tyr-Glu-Glu-Glu-Ile-Arg-Val-Leu, wherein the amino groups may be present in free or protonated form and the carboxy groups may be present in free or deprotonated form and the oligopeptide B comprises the amino acid sequence Tyr-Glu-Glu-Glu-Ile-Arg-Val-Leu, wherein the amino groups may be present in free or protonated form and the carboxy groups may be present in free or deprotonated form.

Especially preferred hair treatment agents of this last-mentioned embodiment contain, based on the total weight of the agent, about 0.00001 to about 1 wt % oligopeptide A and about 0.00001 to about 1 wt % oligopeptide B.

Further preferred hair treatment agents of this last-mentioned embodiment contain, based on the total weight of the agent, about 0.00005 to about 0.1 wt % oligopeptide A and about 0.00005 to about 0.1 wt % oligopeptide B.

Still further preferred hair treatment agents of this last-mentioned embodiment contain, based on the total weight of the agent, about 0.0001 to about 0.01 wt % oligopeptide A and about 0.0001 to about 0.001 wt % oligopeptide B.

The oligopeptides as contemplated herein that meet the aforementioned conditions may advantageously be obtained from keratinous materials. As contemplated herein, it is preferred for these oligopeptides to be used in high proportions relative to the total keratinous peptide content of the agents.

It is especially preferred for the highest possible proportion of all of the keratinous peptides contained in the agent contemplated herein to meet the aforementioned conditions.

Preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Glu-Glu-Glu.

Further preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Glu-Glu-Glu-Ile.

Still further preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Tyr-Glu-Glu-Glu.

Particularly preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Tyr-Glu-Glu-Glu-Ile.

Especially preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Tyr-Glu-Glu-Glu-Ile-Arg.

Still further preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Tyr-Glu-Glu-Glu-Ile-Arg-Val.

Particularly preferred hair treatment agents as contemplated herein are characterized in that at least about 0.1 wt %, preferably at least about 0.5 wt %, particularly preferably at least about 1 wt %, further preferably at least about 2.5 wt %, still further preferably at least about 5 wt %, and, in particular, at least about 10 wt % of all of the keratinous peptides contained in the agent comprise the amino acid sequence Tyr-Glu-Glu-Glu-Ile-Arg-Val-Leu.

The aforementioned conditions relate to the total content of peptides originating from keratinous materials in the agent contemplated herein. In addition to the oligopeptides of keratinous origin, it is also possible, of course, to use other peptides and/or protein hydrolysates, for example, from other native sources. A preferred example is the additional use of wheat protein hydrolysates.

Suitable vitamins are preferably understood to be the following vitamins, provitamins, and vitamin precursors, as well as derivatives thereof:

Vitamin A: The group of substances referred to as vitamin A includes retinol (vitamin $A_1$) and 3,4-didehydroretinol (vitamin $A_2$). R-carotene is the provitamin of retinol. Suitable examples of a vitamin A component are vitamin A acid and esters thereof, vitamin A aldehyde, and vitamin A alcohol and esters thereof, such as palmitate and acetate.

Vitamin B: The vitamin B group or vitamin B complex includes (inter alia)

Vitamin B, (thiamine)

Vitamin B$_2$ (riboflavin)

Vitamin B$_3$. This designation often encompasses the compounds nicotinic acid and nicotinamide (niacinamide).

Vitamin B$_5$ (pantothenic acid and panthenol). Within the framework of this group, it is preferable to use panthenol. Derivatives of panthenol that can be used are, in particular, the esters and ethers of panthenol, pantolactone, and cationically derivatized panthenols. Individual representatives are, for example, panthenol triacetate, panthenol monoethylether, and monoacetate thereof, as well as cationic panthenol derivatives.

Vitamin B$_6$ (pyridoxine, pyridoxamine, and pyridoxal).

Vitamin C (ascorbic acid): Use in the form of the palmitate, glucosides, or phosphates may be preferred. Use in combination with tocopherols may also be preferred.

Vitamin E (tocopherols, in particular, α-tocopherol).

Vitamin F: The term "vitamin F" is generally understood to refer to essential fatty acids, in particular, linoleic acid, linolenic acid, and arachidonic acid.

Vitamin H: The compound (3aS,4S,6aR)-2-oxohexahydrothienol[3,4-d]-imidazole-4-valeric acid is referred to as vitamin H, but the trivial name biotin has now become accepted.

Particularly preferred are vitamins, provitamins, and vitamin precursors from the groups A, B, E, and H. Especially preferred are nicotinamide, biotin, pantolactone, and/or panthenol.

The proportion by weight of the vitamin(s), vitamin derivative(s), and/or vitamin precursor(s) to the total weight of the hair treatment agents is preferably about 0.001 to about 2 wt %, particularly preferably about 0.005 to about 1 wt %, and, in particular, about 0.01 to about 0.5 wt %.

Suitable plant extracts are understood to be extracts which can be produced from all parts of a plant. These extracts are conventionally produced by extraction of the entire plant. It can also be preferable in individual cases, however, to produce the extracts exclusively from flowers and/or leaves of the plant. The extracts from green tea, oak bark, stinging nettle, witch hazel, hops, chamomile, burdock, horsetail, whitethorn, lime blossom, lychee, almond, aloe vera, pine, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, *ginseng*, ginger root, *Echinacea purpurea*, *Olea europaea*, *Boerhavia diffusa* root, *Foeniculum* vulgaris and *Apium graveolens* are suitable above all.

The extracts of green tea, stinging nettle, witch hazel, chamomile, aloe vera, *ginseng, Echinacea purpurea, Olea europaea*, and/or *Boerhavia diffusa* root are particularly preferred for use in the agents contemplated herein.

Water, alcohols, and mixtures thereof can be used as extracting agents to produce the aforementioned plant extracts. Of the alcohols, lower alcohols such as ethanol and isopropanol, but in particular polyhydric alcohols such as ethylene glycol and propylene glycol, are preferred, both as the sole extracting agent and mixed with water. Plant extracts based on water/propylene glycol in the ratio about 1:10 to about 10:1 have proved to be particularly suitable.

The plant extracts can be used in both pure and diluted form. If used in diluted form, they conventionally contain approximately about 2 to about 80 wt % of active substance and, as the solvent, the extracting agent or mixture of extracting agents used to obtain them.

The plant extracts may be used in the hair treatment agents contemplated herein (based on the total weight of the agents) preferably in an amount of about 0.01 to about 10 wt %, more preferably about 0.05 to about 7.5 wt %, and, in particular, about 0.1 to about 5 wt %.

Glycerol may be separately added to the hair cleaning and care agents in an amount of up to about 10 wt % (based on the total weight of the agent). Glycerol may, however, also be a component of the previously mentioned aqueous-alcoholic carrier.

It has been established that the hair treatment agents as contemplated herein are also suitable for use as an anti-dandruff preparation.

The total weight of the anti-dandruff agents to the total weight of the hair treatment agents may preferably be about 0.01 to about 10 wt %, more preferably about 0.025 to about 7.5 wt %, especially preferably about 0.05 to about 5 wt %, and, in particular, about 0.075 to about 3 wt %.

Suitable anti-dandruff substances may be selected from piroctone olamine, climbazole, zinc pyrithione, ketoconazoles, salicylic acid, sulfur, selenium sulfide, tar preparations, undecenoic acid derivatives, burdock extracts, poplar extracts, stinging nettle extracts, walnut shell extracts, birch extracts, willow bark extracts, rosemary extracts, and/or *arnica* extracts.

Climbazole, zinc pyrithione, and piroctone olamine are preferred.

Examples of further active ingredients, auxiliary substances, and additives that can be included in the hair treatment agents contemplated herein include:

humectants, perfumes,

UV filters, thickening agents such as gelatins or plant gums, for example agar-agar, guar gum, alginates, xanthan gum, gum arabic, karaya gum, carob seed meal, linseed gums, dextrans, cellulose derivatives, for example methyl cellulose, hydroxyalkyl cellulose, and carboxymethyl cellulose, starch fractions and derivatives such as amylose, amylopectin, and dextrins, clays and phyllosilicates such as, for example, bentonite or fully synthetic hydrocolloids such as, for example, polyvinyl alcohol, the Ca, Mg, or Zn soaps, texturizing agents such as maleic acid and lactic acid, dimethyl isosorbide, cyclodextrins, active ingredients to improve the fiber structure, in particular mono-, di- and oligosaccharides such as, for example, glucose, galactose, fructose, fruit sugar, and lactose, dyes to color the agent, active ingredients such as bisabolol and/or allantoin, complexing agents such as EDTA, NTA, β-alanine diacetic acid, and phosphonic acids, ceramides. Ceramides are understood to be N-acyl sphingosine (fatty acid amides of sphingosine) or synthetic analogs of such lipids (known as pseudoceramides), propellants such as propane-butane mixtures, N$_2$O, dimethyl ether, CO$_2$, and air, antioxidants, additional viscosity adjusters such as salts (NaCl).

The agents contemplated herein are preferably so-called rinse-off products, i.e., are rinsed out of the hair after a certain contact time. The contact time preferably amounts to less than one hour, i.e., the consumer preferably does not leave the products in the hair until the next hair wash.

Another embodiment contemplated herein is therefore a method for hair treatment, in which an agent as contemplated herein is applied to dry or damp hair, left there for a duration of about 30 to about 300 seconds, and then rinsed out.

The agents as contemplated herein lead to a significantly enhanced stability of artificial dyes against the washing out of color. Thus, with the agents contemplated herein, chemically dyed hair can be washed significantly more often, without leading to an undesired bleeding out or fading of the color.

Another embodiment contemplated herein is therefore use of agents contemplated herein in order to reduce the washing out of color from chemically dyed hair.

What has been stated regarding the agents as contemplated herein also applies, mutatis mutandis, to preferred embodiments of the method contemplated herein and the use contemplated herein.

EXAMPLES

All values represent wt %
Series 1 of Hair Shampoos

|  | 1 | 2 | 3 | 4 | 5 | 6 |
|---|---|---|---|---|---|---|
| $C_{14-16}$ α-olefin sulfonate, sodium salt (AS) | 6.0 | 6.0 | 6.0 | 6.0 | 6.0 | 6.0 |
| Cocoamidopropyl betaine (AS) | 5.0 | 5.0 | 5.0 | 5.0 | 5.0 | 5.0 |
| Sodium methyl cocoyl taurate | 2.0 | 2.0 | 2.0 | 2.0 | 2.0 | 2.0 |
| Polyquaternium 10 | 0.3 | 0.3 | 0.3 | 0.3 | 0.3 | 0.3 |
| PEG-7 glyceryl cocoate | 1.0 | 1.0 | 1.0 | 1.0 | 1.0 | 1.0 |
| Amodimethicone | 0.8 | 0.8 | 0.8 | 0.8 | 0.8 | 0.8 |
| Hydrolyzed Keratin | 0.3 | 0.3 | 0.3 | 0.3 | 0.3 | 0.3 |
| Silver citrate | 0.15 | 0.15 | 0.15 | 0.15 | 0.15 | 0.15 |
| Citric acid | 0.5 | 0.5 | 0.5 | 0.5 | 0.5 | 0.5 |
| Panthenol | 0.5 | 0.5 | 0.5 | 0.5 | 0.5 | 0.5 |
| Laureth-2 | 1.2 | 1.2 | 1.2 | 1.2 | 1.2 | 1.2 |
| Sodium chloride | 1.3 | 1.3 | 1.3 | 1.3 | 1.3 | 1.3 |
| PEG-120 methyl glucose dioleate | 0.7 | 0.7 | 0.7 | 0.7 | 0.7 | 0.7 |
| o-Cymen-5-ol | — | 0.1 | 0.1 | 0.1 | 0.1 | 0.1 |
| Ethyl lauroyl arginate | — | 0.4 | 0.3 | 0.2 | 0.1 | 0.05 |
| Glutaraldehyde | — | 0.05 | 0.06 | 0.07 | 0.08 | 0.1 |
| Dimethyloxazolidine | — | 0.05 | 0.06 | 0.07 | 0.08 | 0.1 |
| Phenoxyethanol | — | 0.05 | 0.05 | 0.05 | 0.05 | 0.05 |
| Phenoxyisopropanol | — | 1.0 | 0.5 | 0.25 | 0.2 | 0.1 |
| Hexetidine | — | 0.1 | 0.05 | 0.1 | 0.05 | 0.1 |
| o-Phenylphenol | — | 0.2 | 0.1 | 0.2 | 0.1 | 0.1 |
| Propionic acid | — | 0.05 | 0.1 | 0.25 | 0.05 | 0.05 |
| Undecylenic acid | — | 0.1 | 0.2 | 0.1 | 0.2 | 0.1 |
| Dye | 0.2 | 0.2 | 0.2 | 0.2 | 0.2 | 0.2 |
| Perfume | 0.1 | 0.1 | 0.1 | 0.1 | 0.1 | 0.1 |
| Water | up to 100% | | | | | |

Series 2 of Hair Shampoos

|  | 1 | 2 | 3 | 4 | 5 | 6 |
|---|---|---|---|---|---|---|
| $C_{14-16}$ α-olefin sulfonate, sodium salt (AS) | 8.0 | 8.0 | 8.0 | 8.0 | 8.0 | 8.0 |
| Disodium cocoamphodiacetate (AS) | 4.0 | 4.0 | 4.0 | 4.0 | 4.0 | 4.0 |
| Sodium methyl cocoyl taurate | 4.0 | 4.0 | 4.0 | 4.0 | 4.0 | 4.0 |
| Cocamide MEA (AS) | 0.3 | 0.3 | 0.3 | 0.3 | 0.3 | 0.3 |
| Guar Hydroxypropyl Trimonium Chloride | 0.1 | 0.1 | 0.1 | 0.1 | 0.1 | 0.1 |
| Panthenol | 0.5 | 0.5 | 0.5 | 0.5 | 0.5 | 0.5 |
| Nicotinamide | 0.3 | 0.3 | 0.3 | 0.3 | 0.3 | 0.3 |
| Dimethicone | 0.8 | 0.8 | 0.8 | 0.8 | 0.8 | 0.8 |
| PEG-7 glyceryl cocoate | 1.0 | 1.0 | 1.0 | 1.0 | 1.0 | 1.0 |
| Silver citrate | 0.3 | 0.3 | 0.3 | 0.3 | 0.3 | 0.3 |
| Citric acid | 0.5 | 0.5 | 0.5 | 0.5 | 0.5 | 0.5 |
| PEG-120 methyl glucose dioleate | 0.7 | 0.7 | 0.7 | 0.7 | 0.7 | 0.7 |
| o-Cymen-5-ol | — | 0.06 | 0.06 | 0.06 | 0.06 | 0.06 |
| Ethyl lauroyl arginate | — | 0.4 | 0.3 | 0.2 | 0.1 | 0.05 |
| Glutaraldehyde | — | 0.05 | 0.06 | 0.07 | 0.08 | 0.1 |
| Dimethyloxazolidine | — | 0.05 | 0.06 | 0.07 | 0.08 | 0.1 |
| Phenoxyethanol | — | 0.05 | 0.05 | 0.05 | 0.05 | 0.05 |
| Phenoxyisopropanol | — | 1.0 | 0.5 | 0.25 | 0.2 | 0.1 |
| Hexetidine | — | 0.1 | 0.05 | 0.1 | 0.05 | 0.1 |
| o-Phenylphenol | — | 0.2 | 0.1 | 0.2 | 0.1 | 0.1 |
| Propionic acid | — | 0.05 | 0.1 | 0.25 | 0.05 | 0.05 |
| Undecylenic acid | — | 0.1 | 0.2 | 0.1 | 0.2 | 0.1 |
| Dye | 0.2 | 0.2 | 0.2 | 0.2 | 0.2 | 0.2 |
| Perfume | 0.1 | 0.1 | 0.1 | 0.1 | 0.1 | 0.1 |
| Water | up to 100% | | | | | |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A hair shampoo consisting of:
a $C_{14-16}$ α-olefin sulfonate, sodium salt present in an amount of 6 weight percent;
Cocoamidopropyl betaine present in an amount of 5 weight percent;
Sodium methyl cocoyl taurate present in an amount of 2 weight percent;
Polyquaternium 10 present in an amount of 0.3 weight percent;
PEG-7 glyceryl cocoate present in an amount of 1 weight percent;
Amodimethicone present in an amount of 0.8 weight percent;
Hydrolyzed keratin present in an amount of 0.3 weight percent;
Silver citrate present in an amount of 0.15 weight percent;
Citric acid present in an amount of 0.5 weight percent;
Panthenol present in an amount of 0.5 weight percent;
Laureth-2 present in an amount of 1.2 weight percent;
Sodium chloride present in an amount of 1.3 weight percent;
PEG-120 methyl glucose dioleate present in an amount of 0.7 weight percent;
Dye present in an amount of 0.2 weight percent;
Perfume present in an amount of 0.1 weight percent; and
a balance of water such that the total weight of all components is 100 weight percent.

2. A hair shampoo consisting of:
a $C_{14-16}$ α-olefin sulfonate, sodium salt present in an amount of 6 weight percent;
Cocoamidopropyl betaine present in an amount of 5 weight percent;
Sodium methyl cocoyl taurate present in an amount of 2 weight percent;
Polyquaternium 10 present in an amount of 0.3 weight percent;
PEG-7 glyceryl cocoate present in an amount of 1 weight percent;
Amodimethicone present in an amount of 0.8 weight percent;
Hydrolyzed keratin present in an amount of 0.3 weight percent;
Silver citrate present in an amount of 0.15 weight percent;
Citric acid present in an amount of 0.5 weight percent;
Panthenol present in an amount of 0.5 weight percent;
Laureth-2 present in an amount of 1.2 weight percent;
Sodium chloride present in an amount of 1.3 weight percent;
PEG-120 methyl glucose dioleate present in an amount of 0.7 weight percent;
o-Cymen-5-ol present in an amount of 0.1 weight percent;
Ethyl lauroyl arginate present in an amount of 0.05 to 0.4 weight percent;
Glutaraldehyde present in an amount of 0.05 to 0.1 weight percent;
Dimethyloxazolidine present in an amount of 0.05 to 0.1 weight percent;
Phenoxyethanol present in an amount of 0.05 weight percent;
Phenoxyisopropanol present in an amount of 0.1 to 1 weight percent;
Hexetidine present in an amount of 0.05 to 0.1 weight percent;
o-Phenylphenol present in an amount of 0.1 to 0.2 weight percent;
Propionic acid present in an amount of 0.05 to 0.25 weight percent;
Undecylenic acid present in an amount of 0.1 to 0.2 weight percent;
Dye present in an amount of 0.2 weight percent;
Perfume present in an amount of 0.1 weight percent; and
a balance of water such that the total weight of all components is 100 weight percent.

3. A hair shampoo consisting of:
C14-16 α-olefin sulfonate, sodium salt present in an amount of 8.0 weight percent;
Disodium cocoamphodiacetate present in an amount of 4.0 weight percent;
Sodium methyl cocoyl taurate present in an amount of 4.0 weight percent;
Cocoamide monoethanolamine (MEA) present in an amount of 0.3 weight percent;
Guar hydroxypropyl trimonium chloride present in an amount of 0.1 weight percent;
Panthenol present in an amount of 0.5 weight percent;
Nicotinamide present in an amount of 0.3 weight percent;
Dimethicone present in an amount of 0.8 weight percent;
PEG-7 glyceryl cocoate present in an amount of 1.0 weight percent;
Silver citrate present in an amount of 0.3 weight percent;
Citric acid present in an amount of 0.5 weight percent;
PEG-120 methyl glucose dioleate present in an amount of 0.7 weight percent;
Dye present in an amount of 0.2 weight percent;
Perfume present in an amount of 0.1 weight percent; and
a balance of water such that the total weight of all components is 100 weight percent.

4. A hair shampoo consisting of:
C14-16 a-olefin sulfonate, sodium salt present in an amount of 8.0 weight percent;
Disodium cocoamphodiacetate present in an amount of 4.0 weight percent;
Sodium methyl cocoyl taurate present in an amount of 4.0 weight percent;
Cocoamide monoethanolamine (MEA) present in an amount of 0.3 weight percent;
Guar Hydroxypropyl Trimonium Chloride present in an amount of 0.1 weight percent;
Panthenol present in an amount of 0.5 weight percent;
Nicotinamide present in an amount of 0.3 weight percent;
Dimethicone present in an amount of 0.8 weight percent;
PEG-7 glyceryl cocoate present in an amount of 1.0 weight percent;
Silver citrate present in an amount of 0.3 weight percent;
Citric acid present in an amount of 0.5 weight percent;
PEG-120 methyl glucose dioleate present in an amount of 0.7 weight percent;
o-Cymen-5-ol present in an amount of 0.06 weight percent;
Ethyl lauroyl arginate present in an amount of from 0.05 to 0.4 weight percent;
Glutaraldehyde present in an amount of from 0.05 to 0.1 weight percent;
Dimethyloxazolidine present in an amount of from 0.05 to 0.1 weight percent;
Phenoxyethanol present in an amount of 0.05 weight percent;
Phenoxyisopropanol present in an amount of from 0.1 to 1 weight percent;
Hexetidine present in an amount of from 0.05 to 0.1 weight percent;

o-Phenylphenol present in an amount of from 0.1 to 0.2 weight percent;
Propionic acid present in an amount of from 0.05 to 0.25 weight percent;
Undecylenic acid present in an amount of from 0.1 to 0.2 weight percent;
Dye present in an amount of 0.2 weight percent;
Perfume present in an amount of 0.1 weight percent; and
a balance of water such that the total weight of all components is 100 weight percent.

* * * * *

SEQUENCE LISTING

<160> NUMBER OF SEQ ID NOS: 7

<210> SEQ ID NO 1
<211> LENGTH: 3
<212> TYPE: PRT
<213> ORGANISM: Artificial
<220> FEATURE:
<223> OTHER INFORMATION: Peptide

<400> SEQUENCE: 1

Glu Glu Glu
1

```
<210> SEQ ID NO 2
<211> LENGTH: 4
<212> TYPE: PRT
<213> ORGANISM: Artificial
<220> FEATURE:
<223> OTHER INFORMATION: Peptide

<400> SEQUENCE: 2

Tyr Glu Glu Glu
1

<210> SEQ ID NO 3
<211> LENGTH: 4
<212> TYPE: PRT
<213> ORGANISM: Artificial
<220> FEATURE:
<223> OTHER INFORMATION: Peptide

<400> SEQUENCE: 3

Glu Glu Glu Ile
1

<210> SEQ ID NO 4
<211> LENGTH: 6
<212> TYPE: PRT
<213> ORGANISM: Artificial
<220> FEATURE:
<223> OTHER INFORMATION: Peptide

<400> SEQUENCE: 4

Tyr Glu Glu Glu Ile Arg
1               5

<210> SEQ ID NO 5
<211> LENGTH: 7
<212> TYPE: PRT
<213> ORGANISM: Artificial
<220> FEATURE:
<223> OTHER INFORMATION: Peptide

<400> SEQUENCE: 5

Tyr Glu Glu Glu Ile Arg Val
1               5

<210> SEQ ID NO 6
<211> LENGTH: 8
<212> TYPE: PRT
<213> ORGANISM: Artificial
<220> FEATURE:
<223> OTHER INFORMATION: Peptide

<400> SEQUENCE: 6

Tyr Glu Glu Glu Ile Arg Val Leu
1               5

<210> SEQ ID NO 7
<211> LENGTH: 9
<212> TYPE: PRT
<213> ORGANISM: Artificial
<220> FEATURE:
<223> OTHER INFORMATION: Peptide

<400> SEQUENCE: 7

Leu Tyr Glu Glu Glu Ile Arg Val Leu
1               5
```